United States Patent
Jia

[11] Patent Number: 6,147,137
[45] Date of Patent: Nov. 14, 2000

[54] DENTAL PRIMER AND ADHESIVE

[75] Inventor: Weitao Jia, Wallingford, Conn.

[73] Assignee: Jeneric/Pentron Incorporated, Wallingford, Conn.

[21] Appl. No.: 09/151,131

[22] Filed: Sep. 10, 1998

[51] Int. Cl.$^7$ ................................................ A61K 6/083
[52] U.S. Cl. .................... 523/118; 524/556; 524/559; 526/318.1; 526/320
[58] Field of Search ............................ 523/118; 524/559, 524/556; 526/318.1, 320

[56] References Cited

U.S. PATENT DOCUMENTS

| | | |
|---|---|---|
| Re. 35,135 | 12/1995 | Sakashita et al. . |
| 4,388,421 | 6/1983 | Suzuki et al. . |
| 4,499,251 | 2/1985 | Omura et al. . |
| 4,636,533 | 1/1987 | Janda et al. . |
| 4,640,936 | 2/1987 | Janda et al. . |
| 4,918,136 | 4/1990 | Kawaguchi et al. . |
| 5,008,300 | 4/1991 | Makino et al. . |
| 5,055,497 | 10/1991 | Okada et al. . |
| 5,089,051 | 2/1992 | Eppinger et al. . |
| 5,145,374 | 9/1992 | Stansbury . |
| 5,177,121 | 1/1993 | Bunker . |
| 5,204,383 | 4/1993 | Manabe et al. . |
| 5,256,447 | 10/1993 | Oxman et al. . |
| 5,294,646 | 3/1994 | Müller et al. . |
| 5,321,053 | 6/1994 | Hino et al. . |
| 5,362,769 | 11/1994 | Waller et al. . |
| 5,498,643 | 3/1996 | Antonucci et al. . |
| 5,534,562 | 7/1996 | Jensen et al. . |
| 5,587,406 | 12/1996 | Yamamoto et al. . |
| 5,645,429 | 7/1997 | Blackwell et al. . |
| 5,658,963 | 8/1997 | Qian et al. . |
| 5,749,733 | 5/1998 | Qian et al. . |
| 5,756,559 | 5/1998 | Blackwell et al. . |
| 5,756,560 | 5/1998 | Antonucci et al. . |
| 5,846,075 | 12/1998 | Suh et al. ................................ 523/118 |

*Primary Examiner*—Andrew E. C. Merriam
*Attorney, Agent, or Firm*—Cantor Colburn LLP

[57] ABSTRACT

A primer/bonding composition for dental restorations comprising a photoinitiator system and a monomer system consisting essentially of at least one polymerizable acidic component and at least one hydrophilic monomer. The presence of a high viscosity monomer such as Bis-GMA is not required. The composition has excellent bonding properties, and is shelf-stable for at least about one year when stored in one container.

18 Claims, No Drawings

DENTAL PRIMER AND ADHESIVE

BACKGROUND OF THE INVENTION

1. Field of the Invention

This invention relates to adhesive compositions for use in composite-based dental restorations. In particular, this invention relates to a simplified, shelf-stable, one-container primer/adhesive dental composition with excellent bonding properties.

2. Brief Discussion of the Prior Art

In the field of dental materials there have recently been developed various primers, adhesives, and primer/adhesive combinations useful for the adhesion of composite dental restorative materials to the tooth. Primers are especially useful for enhancing bonding to dentin after the dentin surface has been cleansed and/or etched. Primers are generally surface-active compounds that exhibit both an affinity for dentine and adhesive resins systems. Primers may participate in the polymerization process, thereby promoting adhesion between the dentine and the adhesive. Known primers include methacrylate-based derivatives of carboxylic acids, phosphoric acids, and derivatives of amino acids such as N-phenylglycine. Especially effective primers include a polymerizable moiety such as a methacrylate, and a surface-active functional moiety such as a carboxylic acid, carboxylic acid anhydride, phosphate, sulfonate, sulfinate, aldehydes, isocyanate, and/or hydroxyl group.

Adhesives are generally in the form of polymerizable resin monomers, for example acrylate and methacrylate-based monomers such as triethylene glycol dimethacrylate (hereinafter TEGDMA), 2-hydroxyethylmethacrylate (hereinafter HEMA), and the like, including viscous resin monomers such as 2,2-bis[p-(2'-hydroxy-3'-methacryloxypropoxy)phenyl]propane (hereinafter Bis-GMA), polyurethane dimethacrylates (hereinafter PUDMA), and the like.

In addition to the above components, dental primer/adhesive compositions may further comprise solvents and curing agents, including chemical, photochemical, and dual-curing free-radical initiators.

There has been increasing interest in "one-container" primer/adhesive compositions, comprising primer, adhesive component, polymerizable resin monomer, and curing agents capable of being provided to the dentist in a pre-mixed, shelf-stable form. Such formulations are convenient for the dentist, as they require no mixing, and primer and adhesive are not required to be applied in two separate steps. Multi-step bonding protocols typical of the current multi-component systems are wasteful of material, and sensitive to technique.

One-container primer/adhesive systems have been disclosed for example in U.S. Pat. Nos. 4,636,533 and 4,640,936 to Janda; and U.S. Pat. Nos. 5,749,733 and 5,658,963 to Qian. Although current adhesive systems such as the foregoing show improvement over their earlier versions, they are still far from ideal. Current systems have complex compositions and application protocols which make dentin bonding an extremely technique-sensitive procedure. Accordingly, there remains a need in the art for improved and simplified one-container dental primer/adhesive compositions with excellent bonding properties.

SUMMARY OF THE INVENTION

The above-described drawbacks and deficiencies of the prior art are alleviated by the simplified primer/adhesive compositions in accordance with the present invention, comprising a photoinitiator system, a solvent system, and a polymerizable monomer system, wherein the monomer system consists essentially of a polymerizable acidic component and a polymerizable hydrophilic component. The absence of a polymerizable high-viscosity component in the monomer system as is taught in the prior art allows enhanced ease of application of the present invention, and results in a stable primer/adhesive composition when pre-mixed and stored in a single container.

Other embodiments of the present invention are a kit including the above-described primer/adhesive composition, and a method of use thereof, i.e., use of the foregoing novel composition as a single step in priming and imparting enhanced adhesion between dental substrates and dental restoratives.

DETAILED DESCRIPTION OF THE INVENTION

The simplified primer/adhesive of the present invention comprises a photoinitiator system, a solvent system, and a monomer system, wherein the monomer system consists essentially of a polymerizable acidic component and a polymerizable hydrophilic component. In an important feature of the present invention, a polymerizable, high-viscosity resin component is not required.

The photoinitiator system of the present invention preferably includes a light-sensitive initiator compound and a polymerization accelerator compound. Light-sensitive initiator compounds are sensitive to UV, or more preferably to visible light, and include, but are not limited to benzophenones, benzoin phenyl ether, and α-diketones such as camphorquinone and camphorquinone derivatives. The light-sensitive initiator compound is generally present in an amount of between about 0.05% to about 2% by weight of the total composition, and preferably in an amount of between about 0.1% to about 1% by weight of the total compositon.

Accelerator compounds which are activated by the initiator compound and which initiate polymerization of the monomer components include but are not limited to tertiary aromatic amines such as ethyl N,N-dimethyl-4-aminobenzoate (hereinafter EDMAB), dimethyl-p-toluidine, dihydroxyethyl-p-toluidine and the like, as well as tertiary amino methacrylates such as dimethylaminoethyl methacrylate, and particularly diethylaminoethyl methacrylate. The accelerator compounds are generally present in an amount of between about 0.05% to about 2% by weight of the total compositon, and preferably between about 0.1% to about 1% by weight of he total composition.

Solvent systems in accordance with the present invention include volatile solvents capable of dissolving the photoinitiator system and the monomer system without adversely reacting with either system or the product. Preferred solvents have boiling points below about 200° C., and include, but are not limited to, water, acetone, ethanol, methyl ethyl ketone, ethyl ether, 1,4-dioxane, ethyl acetate, butyl acetate, hexane, undecane, toluene xylene, methanol, isopropanol, and mixtures of the foregoing.

The amount of solvent will vary depending on the viscosities of the polymerizable compositon, but in general will be present in an amount of between about 10% to about 95% by weight of he total compositon, and preferably in an amount of between about 30% to about 80% by weight of the total compositon.

Polymerizable acidic components of the present invention include monomers having a polymerizable acrylate or methacrylate group and an aromatic carboxylic acid group. Preferred compounds have are aromatic carboxylic acids including but not being limited to biphenyl dimethacrylate (hereinafter BPDM, the reaction product of an aromatic dianhydride with an excess of 2-HEMA as described in U.S. Pat. No. 5,348,988), the reaction product of ethylene glycol is-trimellitate dianhydride with 2-HEMA (hereinafter EDMT), the reaction product of 3,3'4,4'-diphenylsulfone tetracarboxylic dianhydride and 2-HEMA (hereinafter DSDM), the reaction product of pyromellitic dianhydride with 2-HEMA (hereinafter PMDM), the reaction product of pyromellitic dianhydride with glycerol dimethacrylate (hereinafter PMGDM), as well as mixtures of the foregoing products.

The polymerizable acidic component of the present invention is present in an amount of between about 1% to about 60% by weight of the total composition, and preferably in an amount of between about 10% to about 40% by weight of the total compositon.

The polymerizable hydrophilic component of the present invention comprises one or more of those monomers, which when polymerized, forms a polymeric matrix which includes the properties and satisfies the objects of the present invention. Such properties include high mechanical strength of the polymeric material itself, as well as high shear strength associated with strong anchoring to a substrate such as enamel and/or dentin. This corresponds in most instances to substances currently used in dental composites, for adhesive, restorative, sealant, and related purposes, with the exception of certain viscous monomers as outlined below. The polymerizable hydrophilic component includes hydroxyalkyl methacrylates, that is monomers having a polymerizable acrylate or methacrylate group and at least one hydroxyl group. Suitable hydrophilic monomers are selected from low-viscosity monomers known in the art, for example 2-hydroxyethylmethacrylate and 2-hydroxypropylmethacrylate; glyceryl dimethacrylate and; ethyleneglycolmethacrylates, including 1,6-hexanedioldimethacrylate, diethyleneglycolmethacrylate, triethyleneglycolmethacrylate and tetraethyleneglycolmethacrylate; Trimethylolpropane trimethacrylate (hereinafter TMPTMA) is particularly preferred for use in the present invention.

The hydrophilic monomer component is present in an amount of between about 5% to about 80% by weight of the total composition, and preferably in an amount of between about 10% to about 60% by weight of the total composition.

Excluded from the scope of either the polymerizable acidic component or the polymerizable hydrophilic component is high viscosity monomers commonly used in prior art dental primer/adhesive and adhesive formulations. Such high viscosity monomers include the condensation product of bisphenol A and glycidyl methacrylate, 2,2'-bis [4-(3-methacryloxy-2-hydroxy propoxy)-phenyl]-propane (abbreviated "BIS-GMA"), pentaerythritol dimethacrylate ("PEDM"), urethane dimethacrylates ("UDMA"), and the like. Such monomers were considered necessary in order to provide a formulation applicable in one or a relatively few number of coats, and/or to provide a uniform coating. However, the inventors hereof have unexpectedly found that such viscous monomers are not in fact required, and that primer/adhesive systems having excellent application characteristics and excellent bonding strengths may be formulated without use of a high-viscosity monomer.

The composition of the present invention may further comprise various additives known in the art, for example antioxidants such as 6,6-di-tert-butyl-4-methylphenol (hereinafter BHT), Fillers, while generally not used may also be present in amount of up to about 10% by weight. Suitable fillers include inorganic fillers such as fumed silica, colloidal silica, glass, quartz, hydroxyapatite, calcium carbonate, barium sulfate, aluminum oxide, titanium oxide and zirconium oxide, and organic fillers such as polymethyl methacrylate and polystyrene.

All components of the compositions of the present invention are pre-mixed and provided to the practitioner in one container. Such compositions are shelf-stable, that is, do not significantly degrade or react at room temperature after mixing for up to about one year. The compositions are most advantageously provided to the practitioner in the form of a kit, comprising the compositions and an optional etchant (such as phosphoric, citric, nitric, or maleic acid in aqueous solution) and/or a conditioner (such as ethylenediaminetetraacetic acid (EDTA) in aqueous solution).

The compositions are used in the same manner as in the case of previous primer/adhesive compositions. Thus, after the tooth surface is prepared, including an optional acid etch step, the present compositon is applied to the surface with a brush, the solvent is allowed to evaporate, and the composition is at least partially cured. The dental restorative material or other substrate to be adhered is then applied and the composition is fully cured if necessary. More than one layer of the present composition may be applied, with or without curing between application of each layer.

The invention is illustrated by the following non-limiting examples, wherein compositions having the following formulations (parts by weight) were prepared.

| Component | Sample 1 | Sample 2 | Sample 3 |
| --- | --- | --- | --- |
| PMGDM | 13.6 | 17.6 | 15.0 |
| HEMA | 20.0 | 21.0 | 21.0 |
| Bis-GMA | 3.6 | — | 2.0 |
| TMPTMA | 0.9 | 0.5 | — |
| TEGDMA | — | — | 1.0 |
| CQ | 0.45 | 0.45 | 0.45 |
| EDMAB | −45 | 0.45 | — |
| DEAEMA | — | 0 | 0.45 |
| BHT | 0.02 | 0.02 | — |
| $H_2O$ | 3.6 | 2.0 | 3.0 |
| Acetone | 57.38 | 57.98 | 57.1 |

Shear strengths of the bond to dentin of the above adhesive formulations and two commercial formulations (One-Step™ and Prime&Bond™) were measured by the following procedure, wherein freshly extracted molar teeth were mounted into a centering stainless steel ring with self-curing acrylic material. The teeth were sectioned horizontally across the diameter of the tooth using a Buehler-Diamond Saw. The surfaces were polished using 320 grit sandpaper under wet conditions. Each test group used a minimum of 5 teeth (samples). Using 37% phosphoric etching gel from Jeneric/Pentron, the dentin surfaces were etched for 20 seconds and then flushed with copious amount of water for 10 seconds. The dentin surfaces were then gently air dried for two seconds. A one-bottle dentin adhesive was then brushed on to the dentin surface, and within 10 seconds, a second layer of the dentin adhesive was rebrushed on to the surface again to achieve a shiny resin rich surface. The entire surface was then gently air dried and visible light cured for 10 seconds with a Optilux 400 curing light (Demetron Corp.)

The specimens were then mounted on to a Bencor Multi-T Testing Apparatus. One end of its metal sleeve rested on the sample surface and delineated the dimensions of the sample. A 500 gram stabilizer weight rested on the other upper end. The metal sleeve was then filled with Conquest Crystal Composite lot#A23219021 and light cured for 40 seconds on one side and 40 seconds at the opposite side, so that the composite samples of 3.5 mm in diameter and 3.5 mm in length were formed. The specimens were then released from the Bencor Multi-Testing Apparatus and aged for 24 hours in a water bath at 37° C.

The Bencor Multi-T Testing Apparatus was set in a shear testing mode on an Instron Universal Testing Machine. With the specimen in a horizontal position, the specimens ring was carefully inserted from the back of the shear assembly. Care was taken so that the guillotine blade was able to move freely up and down and passively engage the stub on the bonded surface. After the specimen ring was placed in an upright position and tightened, a vertical force was supplied with a cross-head speed of 0.02 inch per minute. The results are listed in the Table below with each standard deviation (S.D.):

| | Shear Bonding Strength to Dentin | | | | |
|---|---|---|---|---|---|
| MPa | One-Step ™ | Prime & Bond ™ | Sample 1 | Sample 2 | Sample 3 |
| (S.D.) | 19.6(3:8) | 18.5(5.6) | 20.5(3.2) | 21.2(1.0) | 19.6(4.9) |

While preferred embodiments have been shown and described, various modifications and substitutions may be made thereto without departing from the spirit and scope of the invention. Accordingly, it is to be understood that the present invention has been described by way of illustrations and not limitation.

What is claimed is:

1. A primer/adhesive dental composition, consisting of
   a photoinitiator system;
   a solvent system; and
   a polymerizable monomer system, wherein the monomer system consists of
      a polymerizable acidic component;
      a polymerizable hydrophilic component selected from the group consisting of 2-hydroxyethylmethacrylate, 2-hydroxypropylmethacrylate, glyceryl dimethacrylate, diethyleneglycolmethacrylate, triethyleneglycolmethacrylate, tetraethyleneglycolmethacrylate, or combinations thereof; and
      trimethylolpropane trimethacrylate, wherein the composition is shelf-stable for at least about one year upon mixing.

2. The composition of claim 1, wherein the photoinitiator system comprises a light-sensitive initiator and a polymerization accelerator.

3. The composition of claim 2, wherein the light-sensitive initiator is camphorquinone, and the polymerization accelerator is ethyl N,N-dimethyl-4-aminobenzoic acid.

4. The composition of claim 1, wherein the polymerizable acidic component is biphenyl dimethacrylate, the reaction product of ethylene glycol bis-trimellitate dianhydride with 2-HEMA, the reaction product of 3,3'4,4'-diphenylsulfone tetracarboxylic dianhydride and 2-HEMA, the reaction product of pyromellitic dianhydride with 2-HEMA, the reaction product of pyromellitic dianhydride with glycerol dimethacrylate, or mixtures thereof.

5. The composition of claim 4, wherein the polymerizable acidic component is the reaction product of pyromellitic dianhydride with glycerol dimethacrylate.

6. The composition of claim 1, wherein
   the polymerizable hydrophilic component is 2-hydroxy ethyl methacrylate.

7. A dental restoration, comprising a primer/adhesive which is shelf-stable for at least about three months upon mixing, wherein the composition consists of
   a photoinitiator system;
   a solvent system; and
   a polymerizable monomer system, wherein the monomer system consists of
      a polymerizable acidic component;
      a polymerizable hydrophilic component selected from the group consisting of
         2-hydroxyethylmethacrylate, 2-hydroxypropylmethacrylate, glyceryl dimethacrylate, diethyleneglycolmethacrylate, triethyleneglycolmethacrylate, tetraethyleneglycolmethacrylate, or combinations thereof; and
      trimethylolpropane trimethacrylate.

8. The dental restoration of claim 7, wherein the photoinitiator system comprises a light-sensitive initiator and a polymerization accelerator.

9. The dental restoration of claim 8, wherein the light-sensitive initiator is camphorquinone, and the polymerization accelerator is ethyl N,N-dimethyl-4-aminobenzoic acid.

10. The dental restoration of claim 7, wherein the polymerizable acidic component is biphenyl dimethacrylate, the reaction product of ethylene glycol bis-trimellitate dianhydride with 2-HEMA, the reaction product of 3,3'4,4'-diphenylsulfone tetracarboxylic dianhydride and 2-HEMA, the reaction product of pyromellitic dianhydride with 2-HEMA, the reaction product of pyromellitic dianhydride with glycerol dimethacrylate, or mixtures thereof.

11. The dental restoration of claim 7, wherein the polymerizable acidic component is the reaction product of pyromellitic dianhydride with glycerol dimethacrylate.

12. The dental restoration of claim 7, wherein the polymerizable hydrophilic component is 2-hydroxy ethyl methacrylate.

13. A method for bonding a dental restoration, comprising applying to a bonding site a primer/adhesive which is shelf-stable for at least about three months upon mixing, wherein the composition consists of
   a photoinitiator system;
   a solvent system; and
   a polymerizable monomer system, wherein the monomer system consists of
      a polymerizable acidic component;
      a polymerizable hydrophilic component selected from the group consisting of
         2-hydroxyethylmethacrylate, 2-hydroxypropylmethacrylate, glyceryl dimethacrylate, diethyleneglycolmethacrylate, triethyleneglycolmethacrylate, tetraethyleneglycolmethacrylate, or combinations thereof; and trimethylolpropane trimethacrylate;
at least partially curing the primer adhesive composition; and
adhering a substrate to the bonding site.

14. The method of claim 13, wherein
the photoinitiator system comprises a light-sensitive initiator and a polymerization accelerator.

15. The method of claim 14, wherein
the light-sensitive initiator is camphorquinone, and the polymerization accelerator is ethyl N,N-dimethyl-4-aminobenzoic acid.

16. The method of claim 13, wherein
the polymerizable acidic component is biphenyl dimethacrylate, the reaction product of ethylene glycol bis-trimellitate dianhydride with 2-HEMA, the reaction product of 3,3'4,4'-diphenylsulfone tetracarboxylic dianhydride and 2-HEMA, the reaction product of pyromellitic dianhydride with 2-HEMA, the reaction product of pyromellitic dianhydride with glycerol dimethacrylate, or mixtures thereof.

17. The method of claim 13, wherein
the polymerizable acidic component is the reaction product of pyromellitic dianhydride with glycerol dimethacrylate.

18. The method of claim 13, wherein
the polymerizable hydrophilic component is a mixture of 2-hydroxy ethyl methacrylate and trimethylolpropane trimethacrylate.

* * * * *

UNITED STATES PATENT AND TRADEMARK OFFICE
CERTIFICATE OF CORRECTION

PATENT NO. : 6,147,137
DATED : November 14, 2000
INVENTOR(S) : Weitao Jia

It is certified that error appears in the above-identified patent and that said Letters Patent is hereby corrected as shown below:

Column 2,
Lines 51 and 64, after "of" delete "he" and insert therefor -- the --

Column 3,
Line 2, after "compounds" delete "have"
Line 56, delete "("PEDM)" and insert -- ("PEDM") --

Column 4,
Line 2, after "BHT)" delete "," and insert therefor -- . --
Line 3, after "in" delete "amount" and insert therefor -- amounts --
Table, line 8, after "EDMAB" delete "-45" and insert therefor -- .45 --

Column 5,
Table, delete

| | Shear Bonding Strength to Dentin | | | | |
|---|---|---|---|---|---|
| MPa | One-Step ™ | Prime & Bond ™ | Sample 1 | Sample 2 | Sample 3 |
| (S.D.) | 19.6(3:8) | 18.5(5.6) | 20.5(3.2) | 21.2(1.0) | 19.6(4.9) | and insert therefor

| | Shear Bonding Strength to Dentin | | | | |
|---|---|---|---|---|---|
| MPa (S.D.) | One-Step™ | Prime & Bond™ | Sample 1 | Sample 2 | Sample 3 |
| | 19.6 (3.8) | 18.5 (5.6) | 20.5 (3.2) | 21.2 (1.0) | 19.6 (4.9) |

Signed and Sealed this

Thirteenth Day of July, 2004

JON W. DUDAS
*Acting Director of the United States Patent and Trademark Office*